US006419695B1

(12) United States Patent
Gabbay

(10) Patent No.: US 6,419,695 B1
(45) Date of Patent: Jul. 16, 2002

(54) CARDIAC PROSTHESIS FOR HELPING IMPROVE OPERATION OF A HEART VALVE

(76) Inventor: Shlomo Gabbay, #1 Randall Dr., Short Hills, NJ (US) 07078

(*) Notice: Subject to any disclaimer, the term of this patent is extended or adjusted under 35 U.S.C. 154(b) by 0 days.

(21) Appl. No.: 09/575,880

(22) Filed: May 22, 2000

(51) Int. Cl.[7] .......... A61F 2/06
(52) U.S. Cl. .......... 623/2.36
(58) Field of Search .......... 623/2.1–2.42

(56) References Cited

U.S. PATENT DOCUMENTS

| | | | | |
|---|---|---|---|---|
| 4,042,979 A | | 8/1977 | Angell | 3/1.5 |
| 4,240,161 A | * | 12/1980 | Huffstutler et al. | 137/527.8 |
| 4,350,492 A | | 9/1982 | Wright et al. | 8/94.11 |
| 4,491,986 A | | 1/1985 | Gabbay | 3/1.5 |
| 4,759,758 A | | 7/1988 | Gabbay | 623/2 |
| 5,258,021 A | * | 11/1993 | Duran | 623/2.36 |
| 5,549,665 A | | 8/1996 | Vesely et al. | 623/2 |
| 5,584,879 A | | 12/1996 | Reimold et al. | 623/2 |
| 5,800,527 A | * | 9/1998 | Jansen et al. | 623/2 |
| 5,861,028 A | | 1/1999 | Angell | 623/2 |

* cited by examiner

*Primary Examiner*—Corrine McDermott
*Assistant Examiner*—Thomas C. Barrett
(74) *Attorney, Agent, or Firm*—Amin & Turocy, LLP

(57) ABSTRACT

An apparatus for helping improve operation of a heart valve includes a generally annular base and a buttress extending generally axially from and inwardly relative to an arc portion of the base. When the apparatus is when implanted at an annulus of a heart valve, the buttress thereof provides a surface with which a leaflet of the heart valve may move into and out of engagement for helping control blood flow relative to the apparatus and heart valve.

29 Claims, 3 Drawing Sheets 25
10
20
26
34
18
14
22
36
12
16

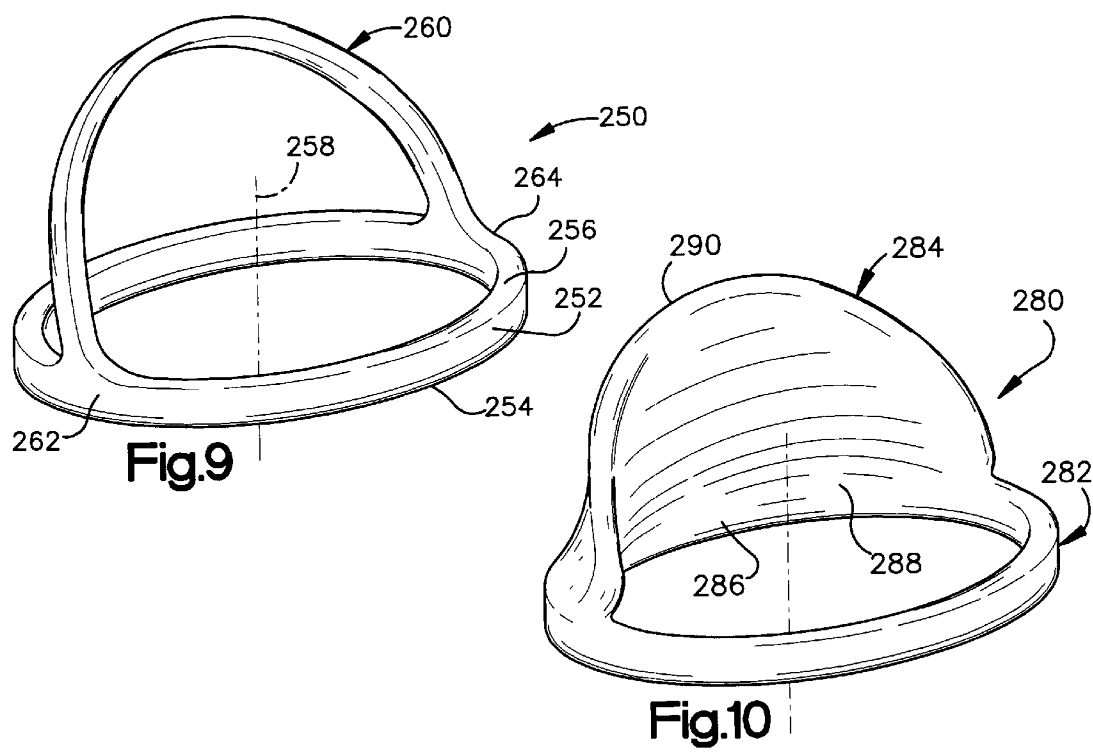
Fig.9
Fig.10
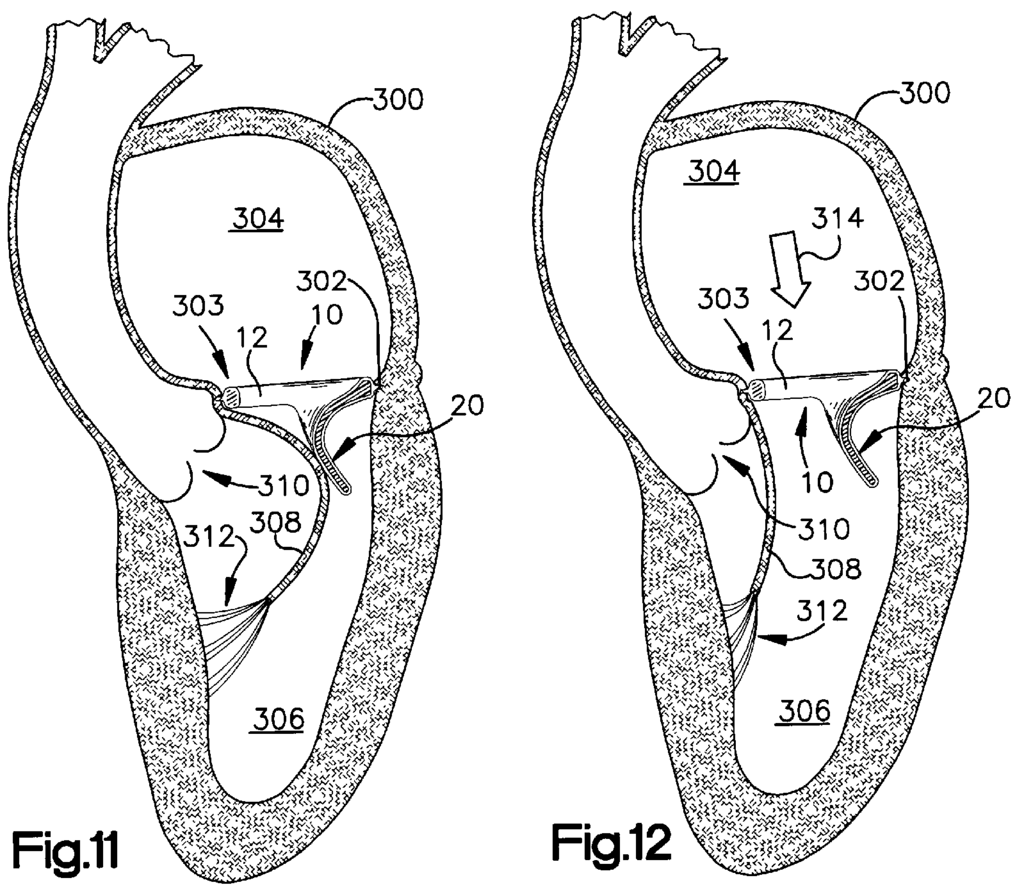
Fig.11
Fig.12

CARDIAC PROSTHESIS FOR HELPING IMPROVE OPERATION OF A HEART VALVE

TECHNICAL FIELD

The present invention relates to an implantable cardiac prosthesis and, more particularly, to a prosthesis that may be implanted at an annulus of a heart valve to help improve operation of a defective or damaged valve.

BACKGROUND

A heart valve may become defective or damaged, such as resulting from congenital malformation, disease, or aging. When the valve becomes defective or damaged, the leaflets may not function properly. One common problem associated with a degenerating heart valve is an enlargement of the valve annulus (e.g., dilation). Other problems that may result in valve dysfunction are chordal elongation and lesions developing on one or more of the leaflets.

The bicuspid or mitral valve is located in the left atrioventricular opening of the heart for passing blood unidirectionally from the left atrium to the left ventricle of the heart. The mitral valve is encircled by a dense fibrous annular ring and includes two valve leaflets of unequal size. A larger valve leaflet, which is known as the anterior leaflet, is located adjacent the aortic opening. The smaller leaflet is the posterior leaflet.

When a mitral valve functions properly, for example, it prevents regurgitation of blood from the ventricle into the atrium when the ventricle contracts. In order to withstand the substantial backpressure and prevent regurgitation of blood into the atrium during the ventricular contraction, the cusps are held in place by fibrous cords (cordae tendinae) that anchor the valve cusps to the muscular wall of the heart.

By way of example, if an annulus enlarges or dilates to a point where the attached leaflets are unable to fully close (malcoaptation), regurgitation or valve prolapse may occur. Adverse clinical symptoms, such as chest pain, cardiac arrhythmias, dyspnea, may manifest in response to valve prolapse or regurgitation. As a result, surgical correction, either by valve repair procedures or by valve replacement, may be required.

Surgical reconstruction or repair procedures may include plication, chordal shortening, or chordal replacement. Another common repair procedure relates to remodelling of the valve annulus (e.g., annuloplasty), which may be accomplished by implantation of a prosthetic ring to help stabilize the annulus and to correct or help prevent valvular insufficiency which may result from defect or dysfunction of the valve annulus. Properly sizing and implanting the annuloplasty ring can substantially restore the valve annulus restored to its normal, undilated, circumference. In situations where the valve leaflets exhibit lesions, it also may be necessary to reconstruct one or more valve leaflets by securing grafts or patches to the leaflets, such as over lesions or holes formed in the leaflet. The repair or reconstruction of the leaflets may be complicated and time consuming, the results of which are not readily reproducible.

SUMMARY

The present invention relates to a cardiac prosthesis that may be implanted at an annulus of a heart valve to help improve operation of a defective or damaged valve. The apparatus includes a base portion, which may be attached to the valve annulus for providing support at the annulus. A buttress portion extends from the base portion, such as in a radially inwardly and generally axially manner. When the apparatus is implanted at an annulus of a heart valve, the buttress provides a surface against which one or more leaflets (depending on the type of heart valve) may move into and out of engagement. When the leaflet engages or coapts with the buttress, flow of blood through the apparatus and valve is inhibited, thereby mitigating regurgitation. The apparatus also permits the flow of blood through the apparatus and valve as the leaflet is urged away from the buttress.

An aspect of the present invention provides an apparatus for helping improve operation of a heart valve. The apparatus includes a generally annular base. A buttress extends generally axially from and inwardly relative to an arc portion of the base for, when implanted, providing a surface with which a leaflet of the heart valve may move into and out of engagement for controlling blood flow relative to the apparatus.

Another aspect of the present invention provides an apparatus for helping improve operation of a heart valve. The apparatus includes a frame having a generally annular base portion and a support portion extending generally axially and inwardly relative to the base portion. The support portion terminates at a distal end spaced from the base portion. A sheath of a flexible material covers the frame to form a buttress extending between the base portion and the distal end of the support portion. As a result, when the apparatus is implanted, the buttress provides a surface with which a leaflet of the heart valve may move into and out of engagement.

To the accomplishment of the foregoing and related ends, the invention, then, comprises the features hereinafter fully described and particularly pointed out in the claims. The following description and the annexed drawings set forth in detail certain illustrative aspects of the invention. These aspects are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

FIG. 9 is an isometric view of a support frame for an apparatus in accordance with another aspect of the present invention;

FIG. 10 is an isometric an apparatus in accordance with another aspect of the present invention, which also may be employed as a frame for an apparatus;

FIG. 11 is a cross-sectional view of part of a heart in which an apparatus, in accordance with the present invention, is mounted at a heart valve, illustrating a first condition of the heart valve; and FIG. 12 is a cross-sectional view of the heart and apparatus, similar to FIG. 11, illustrating a second condition of the heart valve.

DESCRIPTION

Figure 1:
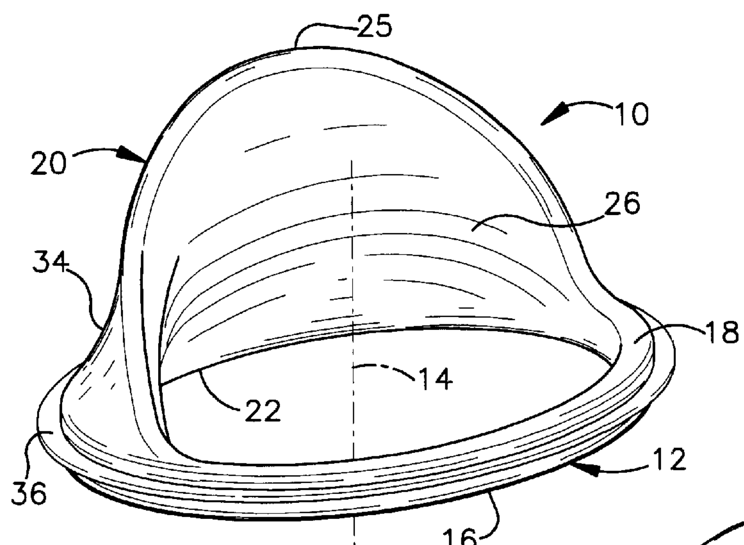
FIG. 1 is an isometric view of an apparatus in accordance with the present invention.
Figure 2:
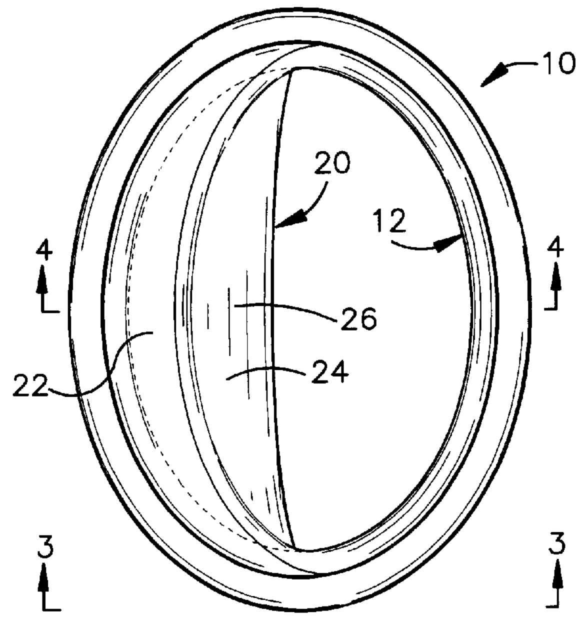
FIG. 2 is an outflow view of an apparatus in accordance with the present invention.

FIGS. 1–4 illustrate an apparatus 10, in accordance with an aspect of the present invention, for helping improve operation of a heart valve. The apparatus 10 includes a generally annular base portion 12, which may be an oval shape, egg-shaped or another suitable shape dimensioned and configured for attachment at an annulus of a heart valve. A central axis 14 extends through the apparatus 10 substantially transverse to a plane extending through the base portion 12. The base portion 12 has an inflow side 16 and an outflow side 18.

The base portion 12 may be formed of a generally rigid or flexible material, such as depending on the desired amount of support for a valve annulus to which the apparatus 10 is to be mounted. For example, the base portion 12 may be a plastic-like material, a metal, or other material suitable for implantation into a patient. The base portion 12 provides the benefits of an annuloplasty ring (e.g., it helps support a valve annulus at a desired orientation at systole).

The apparatus 10 also includes a buttress 20 that is attached to and extends from the base portion 12 for providing a surface against which a leaflet of a heart valve may engage. The buttress 20 is connected to the base portion 12 along a circumferentially extending arc length of the base portion. The arc length of the base portion 12 may approximate the length of annular attachment for a defective or damaged valve leaflet for which the buttress 20 (when the apparatus is implanted) is intended to function.

By way of example, when the apparatus 10 is to be implanted at the annulus of a mitral valve and function in place of a posterior leaflet, the circumferential arc may approximate the length of the annulus adjacent the posterior leaflet of the valve. Additionally, the circumferential length of the sidewall of the buttress 20 approximates the posterior leaflet.

Figure 3:
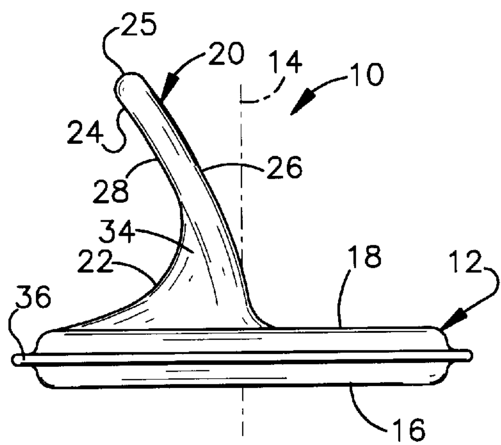
FIG. 3 is a side elevation of an apparatus for supporting a heart valve in accordance with the present invention, taken along line 3—3 of FIG. 2.
Figure 4:
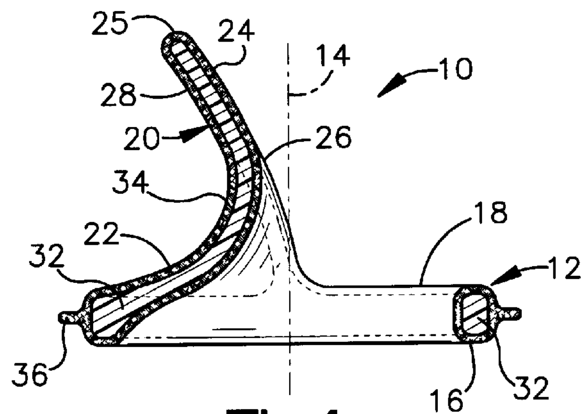
FIG. 4 is a cross-sectional view of the apparatus taken along line 4—4 of FIG. 2.

The buttress 20 extends generally axially from and radially outwardly relative to the outflow side 18 of the base portion 12. An axial length of a portion 22 of the buttress 20 proximal the base portion 12 extends radially inwardly toward the axis 14 and generally axially away from the base portion. A distally extending portion 24 of the buttress 20 extends from the proximal portion 22 and curves radially outwardly therefrom for the remaining length of the buttress to terminate in a distal end 25. The buttress 20 has a radially inner surface 26 that provides a surface against which a leaflet (e.g., an anterior leaflet of a mitral valve) may coapt at systole. As shown in FIGS. 3 and 4, a radially outer surface 28 of the buttress 20 at the distally extending portion 24 has a generally convex or an inverted C-shaped cross-section.

In the example of the apparatus 10 shown in FIGS. 1–4 (having a complete annular base portion 12), an aperture extends axially through the apparatus 10 between another arc length of the base portion 12 and the buttress itself. The aperture provides an opening or orifice to permit the passage of blood through the apparatus 10, such as during diastole. The buttress 20 in conjunction with the leaflet (or leaflets) also inhibits the flow of blood when the valve is in a closed position, such as during ventricular contraction at systole.

The apparatus 10 shown in FIGS. 1–4 includes a support frame 32 that is dimensioned and configured to provide a desired shape for the apparatus 10. The frame 32 provides a support mechanism that forms the base portion 12 and the buttress 20. The frame 32, for example, may be formed of a resilient and/or flexible material, such as a plastic, metal or other material suitable for implantation into a human. The rigidity or flexibility of each part of the frame may vary depending upon the amount of support desired at the annulus (by the base portion) as well as the amount of flexibility desired during engagement between a leaflet and the buttress 20.

Alternatively, the underlying support frame 32 of the buttress 20 and/or the base portion 12 may be formed of a substantially inelastically deformable material (e.g., it is bendable to and remains at a desired position), such as a metal wire. As a result, a surgeon implanting the apparatus 10 may reorient the buttress 20 and/or the base portion 12 to a desired configuration for improving the operation of the valve. Such material also may exhibit sufficient resilience so that it maintains the shape set by the surgeon (or manufacturer) after being implanted and subjected to the dynamics of the heart valve.

The frame parts for the base portion 12 and the buttress 20 may be formed of the same or different materials depending on the material properties (elasticity, rigidity, resilience, etc.) desired for each part of the apparatus 10.

An outer sheath 34 of a biocompatible material covers the frame 32, including the base portion 12 and the buttress 20. The outer sheath 34 may be substantially any material, such as a cloth-like or fabric material (natural or synthetic), a biological material, such as collagen or an animal tissue material. An acceptable animal tissue material is smooth animal pericardium (e.g., equine, bovine, porcine, etc.) that has been tanned or fixed in a suitable tanning environment. The pericardium, for example, is cross-linked with glutaraldehyde and undergoes a detoxification process with heparin bonding, such as one of the NO-REACT® natural tissue products that are commercially available from Shelhigh, Inc. of Millburn, N.J. The NO-REACT® natural tissue products exhibit improved biocompatibility and mitigate calcification and thrombus formation. The exposed smooth animal pericardium covering the buttress 20 further inhibits abrasion that could occur in response to engagement between a leaflet and the buttress.

The apparatus 10 also may include an implantation flange 36 (or sewing ring) that circumscribes the base portion of the apparatus 10. The implantation flange 36 extends radially outwardly from the base portion 12 and provides a structure for facilitating implantation of the apparatus 10 at an annulus of a heart valve. The implantation flange 36 is formed of a flexible material, such a cloth-like or fabric material (natural or synthetic), a biological material, such as collagen, or an animal tissue material. For example, the implantation flange 36 is formed of a substantially biocompatible biological material, such as animal tissue (e.g., animal pericardium). The implantation flange 36 may be formed as an integral part of the outer sheath 34, such as a single or double layer of the material that is used to form the outer sheath.

Figure 5:
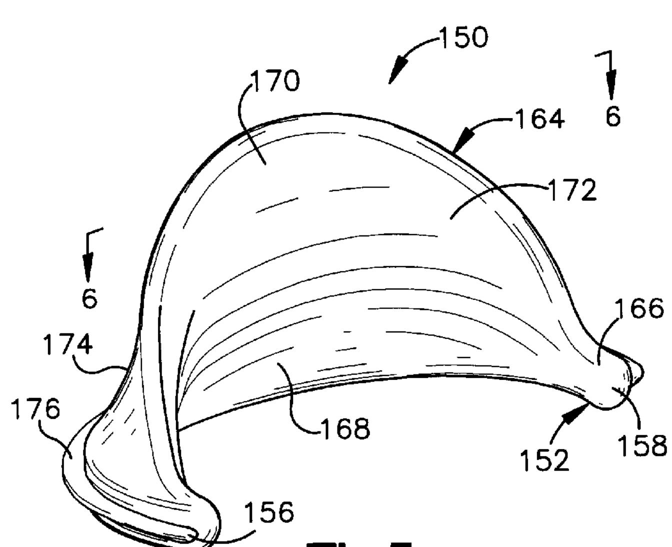
FIG. 5 is an isometric view of an apparatus for supporting a heart valve in accordance with another aspect of the present invention.
Figure 6:
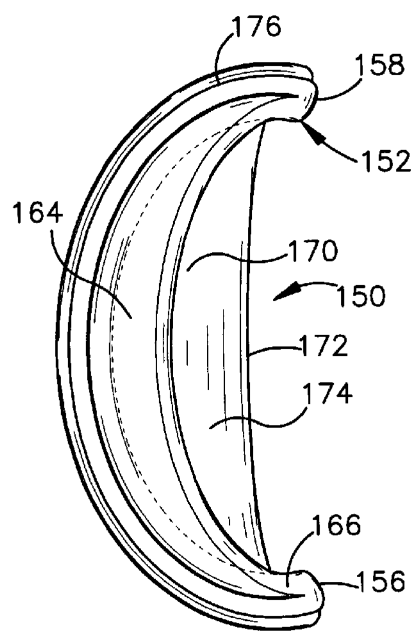
FIG. 6 is a view of the apparatus taken along line 6—6 of FIG. 5.

FIGS. 5 and 6 illustrate a heart valve repair apparatus 150 in accordance with another aspect of the present invention. The apparatus 150 includes a generally annular base portion 152 that is generally C-shaped (or incomplete). The base portion 152 has ends 156 and 158 that are spaced apart from each other and a curved portion extending between the ends.

In this example, the base portion 152 includes an underlying C-shaped support ring, which may be formed of a flexible, resilient, or generally rigid material. The support ring may have an elastic property so as to return to its original shape when deflected from its original (or rest) condition. The support ring for example, may be a plastic-like material (e.g., a polymer, a resin, etc.) or a metal (e.g., stainless steel), such as in the form of a wire. It will be understood and appreciated that other types of generally rigid, elastic, and/or resilient materials also may be used in accordance with the present invention. In addition, a suitable inelastically deformable material also could be used to form the support ring.

A buttress 164 extends generally axially from an outflow side 166 of the base portion 152 in a manner that is substantially similar to that shown and described with respect to FIGS. 1–4. Briefly stated, a proximal portion 168 of the buttress 164 extends generally axially and radially inward from the base portion 152 toward an open end (between ends 156 and 158) of the base portion. A distally extending portion 170 of the buttress 164 extends from the proximal portion 168 and curves radially outwardly therefrom for the remaining length of the buttress. The buttress 164 has a radially inner surface 172 that provides a surface against which a leaflet (e.g., an anterior leaflet of a mitral valve) may coapt at systole. The buttress 164 is dimensioned and configured to simulate the dimensions and configuration of a leaflet at systole so that, when the apparatus 150 is implanted at an annulus of a heart valve, a leaflet (or leaflets) may engage the buttress 164 to close the valve at systole. The leaflet (or leaflets) is able to coapt with the inner surface 172 of the buttress 164 at systole, thereby inhibiting regurgitation of blood when the ventricle contracts.

As in the example of FIGS. 1–4, the apparatus 150 also includes an outer sheath 174 of a flexible, biocompatible material covering the apparatus. The apparatus 150 also may include an implantation flange 176 (or sewing ring) that circumscribes the base portion 152 of the apparatus. The implantation flange 176 extends radially outwardly from the base portion 12 between the ends 156 and 158 for facilitating implantation of the apparatus 150 at an annulus of a heart valve. Each of the outer sheath 174 and the implantation flange 176 may be formed of any suitable flexible, biocompatible material, such as a cloth-like or fabric (natural or synthetic) material, a biological material, such as collagen or an animal tissue material. An acceptable animal tissue material is smooth animal pericardium (e.g., equine, bovine, porcine, etc.), such as a NO-REACT® tissue product.

Figure 7:
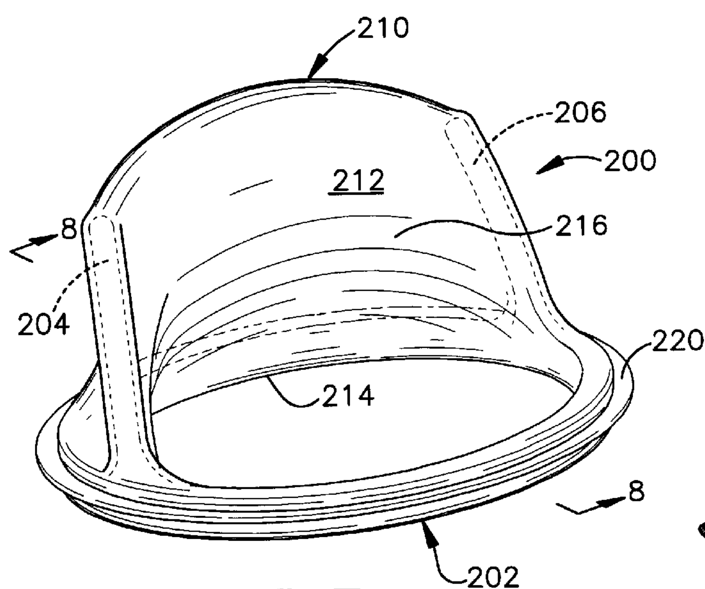
FIG. 7 is an isometric view of an apparatus in accordance with another aspect of the present invention.
Figure 8:
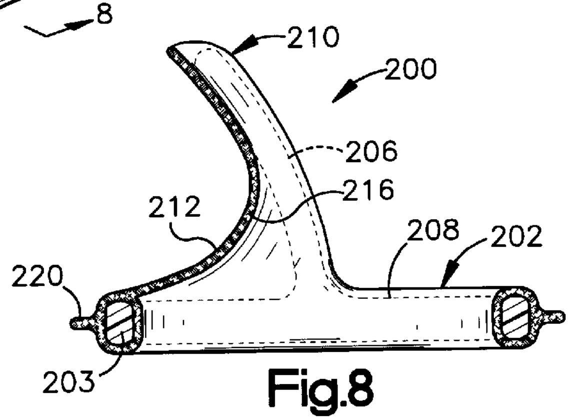
FIG. 8 is a cross-sectional view of the apparatus taken along line 8—8 of FIG. 7.

FIGS. 7 and 8 illustrate a heart valve repair apparatus 200 in accordance with another aspect of the present invention. The apparatus 200 includes a generally annular base portion 202. The base portion 202 includes a support ring 203 that is dimensioned and configured to approximate the dimensions and configuration of a heart valve annulus, such as a mitral or atrioventricular valve. The support ring 203 may be substantially similar to that disclosed with respect to the base portions shown and described with respect to FIGS. 1–6 (e.g., it may be a complete ring (as shown) or a generally C-shaped ring).

A pair of support posts 204 and 206 extend generally axially from an outflow side 208 of the base portion 202. The supports 204 and 206 are circumferentially spaced apart from each other an arc length that approximates the circumferential dimension of a valve leaflet for which the apparatus 200 is intended to function. The support posts 204 and 206 may be formed of the same material or a different material as that which forms the base portion 202. For example, the support posts 204 and 206 and the base portion 202 may be formed as an integral unit in a suitable injection molding process. It is to be appreciated, however, that different materials also may be utilized to form the supports 204 and 206 and the base portion 202, with the supports being appropriately secured to the base portion, such as by ultrasonic welding or another method of attachment.

The apparatus 200 also includes a buttress 210 of a substantially flexible material that extends generally axially from the base portion 202 for providing a flexible surface for abutment with an adjacent leaflet of a heart valve. The buttress 210, for example, includes a flexible sheet 212 of material that is attached to the base portion 202 along a circumferentially extending arc 214 between the juncture of each of the support posts 204 and 206 and the base portion. The flexible sheet 212 of material extends generally axially from the base portion 202 and is connected to and extends between the support posts 204 and 206. The support posts 204 and 206 may be linear or curved to orient the sheath of flexible material connected therebetween at a desired position for engaging an adjacent leaflet. The sheet 212 of flexible material also may cover each of the support posts 204 and 206 as well as the annular base portion 202 so as to completely cover the frame, which is formed of the base portion and support posts. The sheet 212 of flexible material of the buttress 210 provides a radially inner surface 216 with which an adjacent leaflet may move into and out of engagement when the apparatus 200 is implanted. The flexible sheath 212 of material also may permit flexible movement of the buttress 210 relative to the supports 204 and 206, such that when the apparatus is implanted it facilitates coaptation between an adjacent leaflet (or leaflets) and the buttress.

As mentioned above with respect to the apparatus of FIGS. 1–4, the posts 204 and 206 and/or the base portion 202 may be formed of an inelastically deformable material. A surgeon implanting the apparatus 200, thus, may bend the buttress 210 and/or base portion 202 to a desired configuration. As a result, each apparatus may be customized for a patient so as to improve the operation of a heart valve when the apparatus 200 is implanted at the valve annulus.

The sheet 212 of flexible material, for example, may be a cloth or fabric material (natural or synthetic), a biological material, such as a sheet of collagen material or an animal tissue material, such as animal pericardium. In order to inhibit regurgitation of blood when implanted at a heart valve, the flexible sheath 212 of material should be substantially impervious to the flow of blood therethrough.

As illustrated in FIGS. 7 and 8, the apparatus also may include an implantation flange (or sewing ring) 220 for facilitating implantation of the apparatus at an annulus of a heart valve. The implantation flange 220 extends radially outwardly from the base portion 202. The implantation flange 220 is formed of a flexible material, such a cloth-like or fabric material (natural or synthetic), or a biological material, such as collagen or an animal tissue material. For example, the implantation flange 220 is formed of a biocompatible biological material, such as animal tissue (e.g., animal pericardium), which is the same material that forms the outer sheath 212.

FIG. 9 illustrates a frame 250 that may be employed to form an apparatus for helping repair a heart valve in accordance with another aspect of the present invention. For example, the frame 250 may be used to form an apparatus of a type similar to that shown and described with respect to FIGS. 1–4. The frame 250 provides a skeleton over which an outer sheath of a substantially flexible material may be applied.

The frame 250 includes a generally annular base portion 252. While the base portion 252 is illustrated as a complete ring, it will be understood and appreciated by those skilled in the art that an incomplete ring (e.g., a C-shaped ring) alternatively may be utilized in accordance with an aspect of the present invention. The base portion 252 includes an inflow side 254, and outflow side 256, with a central axis 258 extending through the base portion.

The frame 250 also includes a support 260 extending generally axially from the base portion 252. The axially extending support 260 is in the form of a curved structure that connects substantially opposed edges 262 and 264 of the base portion 252 for providing a support structure for a buttress.

The frame 250, for example, may be formed of a resilient material, a flexible material, or an inelastically deformable material, such as a plastic, a metal, or other material suitable for implantation into a human. The rigidity or flexibility of a material utilized to form the frame 250 may vary depending upon the amount of support desired at the annulus (by the base portion) as well as the amount of flexibility desired during coaptation between a leaflet and the buttress. The base portion 252 and the axially extending support 260 may be formed of the same or different materials, depending on the material properties (elasticity, rigidity, resilience, etc.) desired for each part of the frame 250.

The frame 250 may be covered with a sheet of a substantially flexible material to form an apparatus, similar to that shown and described with respect to FIGS. 1–4. A sheet of flexible material is applied over the frame so that the flexible material may be moveable relative to the axially extending support 260, such as in response to an adjacent leaflet moving into engagement with the overlying sheet of material. In contrast, the illustrated apparatus of FIGS. 1–4 employs a frame that includes a substrate material coextensive with the buttress onto which the sheet of flexible material is applied (e.g., the buttress of FIGS. 1–4 may be more static than the flexible buttress of FIG. 9).

FIG. 10 illustrates a heart valve repair apparatus 280 in accordance with another aspect of the present invention. Similar to the apparatus 10 of FIG. 1, the apparatus 280 includes a generally annular base portion 282 that is dimensioned and configured according to the dimensions and configuration of a heart valve annulus to which the apparatus is to be attached. As mentioned above with respect to FIGS. 1–4, the flexibility or resilience or rigidity of the base portion 282 may vary according to the material used to form the base portion, such as to provide a desired amount of support at the heart valve annulus.

A buttress 284 is attached to and extends radially inwardly and generally axially away from a posterior arc 286 of the base portion 282. More specifically, a proximal portion 288 of the buttress 284 extends axially and radially inwardly over a first portion of its length. A remaining portion 290 of the buttress 284 extends distally from the proximal portion 288 and curves radially outwardly relative to (or away from) the proximal portion. When the apparatus 280 is implanted, the buttress 284 provides a surface with which an adjacent leaflet may move into and out of engagement.

The apparatus 280 may be formed of a flexible and/or resilient material, such as a polymer or plastic-like material (e.g., Delrin®, pyrolythic carbon, etc.), a metal, or other material considered appropriate for implantation into a heart. The base portion 282 and the buttress 284, for example, may be formed of the same material to form an integral apparatus. Alternatively, different materials may be utilized to form each of the buttress 284 and the base portion 282, such as when different amounts of rigidity or flexibility may be desired for each respective part.

It will be understood and appreciated that the apparatus 280 further may be employed as the underlying frame 32 of the apparatus 10, as shown and described with respect to FIGS. 1–4. In order to form the apparatus 10 from the apparatus 280, an outer sheath of an appropriate flexible, biocompatible material is mounted over the apparatus 280, such as set forth above.

FIGS. 11 and 12 illustrate part of a heart 300 in which an apparatus, such as the apparatus 10 illustrated with respect to FIGS. 1–4, is implanted at an annulus 302 of a mitral valve 303. The mitral valve 303 is intended to provide for the unidirectional flow of blood from the left atrium 304 into the left ventricle 306. The mitral valve 303 includes an anterior leaflet 308 that extends from the annulus 302 adjacent the aortic opening 310 and attaches to the muscular tissue in the wall of the left ventricle by fibrous cordae tendinae 312. The posterior leaflet has been substantially removed from the heart, such as by excising it prior to implantation of the apparatus 10. It is to be understood and appreciated, however, that the posterior leaflet may remain intact, with a buttress 20 of the apparatus 10 interposed between the posterior and anterior leaflets.

As mentioned above, the apparatus 10 may include an implantation flange 36 that is sutured to the fibrous tissue at the annulus 302 of the valve 303. The buttress 20 extends from the base 12 of the apparatus 10 into the ventricle 306 at a position corresponding to the position of the posterior leaflet of the mitral valve 303. As mentioned above, the buttress 20 extends into the ventricle 306 generally toward the posterior leaflet 308.

It is to be appreciated that the buttress 20 may be formed of a generally rigid material that remains substantially stationary (e.g., static) during both systole and diastole. Alternatively, the buttress 20 may be a sufficiently flexible material, such as a sheet of material supported in a peripheral frame (see, e.g., FIGS. 7–9) or by employing a more flexible type of frame to permit movement thereof commensurate with the flow of blood from the atrium 304 into the ventricle 306 through the valve 303.

FIG. 11 illustrates the mitral valve 303 is in a closed position (at systole), in which the anterior leaflet 304 engages the buttress 20 of the apparatus 10 in accordance with an aspect of the present invention. That is, the buttress 20 of the apparatus 10 simulates the function of the posterior leaflet at systole by providing a surface against which the anterior leaflet 308 coapts. As a result, the buttress 20 and the anterior leaflet 304 cooperate to inhibit regurgitation of blood from the left ventricle 308 into the left atrium 306, such as during ventricular contraction at systole.

The buttress 20 in conjunction with the anterior leaflet also facilitates and promotes unidirectional flow of blood at diastole, such as shown in FIG. 11 by arrow 314. In particular, an opening or aperture extends through the implanted apparatus 10 between the buttress 20 and the anterior leaflet 308. Advantageously, the movement of the anterior leaflet 308 relative to the buttress 20, in response to the flow of blood during diastole, provides a sufficient orifice to permit the free flow of blood from the left atrium 304 into the left ventricle 306. The buttress 20 also may be formed of a flexible material that is able to move radially relative to the base portion 12 to further facilitate blood flow. The annular base portion 12 of the apparatus 10 also may help support the annulus 302 of the mitral valve 303 at systole to promote the desired coaptation between the buttress 20 and the anterior leaflet 308 (FIG. 10).

In view of the foregoing, an apparatus according to the present invention provides a useful repair apparatus for helping to improve operation of a heart valve. The apparatus may be employed to both support a heart valve annulus and mitigate problems associated with coaptation and/or lesions in a leaflet by providing a buttress with which one or more leaflets may move into and out of engagement. The apparatus further provides a simplified repair option (implanting a device at an annulus of a heart valve) when compared with other, more conventional methods of reconstruction and repair.

It is to be appreciated by those skilled in the art that, while the illustrated examples show the apparatus for treating a bicuspid (mitral) valve, an apparatus in accordance with the present invention also may be used for repairing other types of heart valves (e.g., a tricuspid valve or other bicuspid valves). In addition, an apparatus may in accordance with the present invention, be implanted at either the inflow side or outflow side of a heart valve annulus.

What has been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising."

What is claimed is:

1. An apparatus for helping improve operation of a heart valve, comprising:

a generally arcuate base portion; and a buttress extending generally radially inwardly and axially relative to the base portion so as to permit substantially bi-directional flow of blood axially relative to the apparatus, the buttress having a surface dimensioned and configured to be engaged by at least one leaflet of the heart valve when the apparatus is implanted at the heart valve, whereby when the apparatus is implanted at the heart valve, movement of the at least one leaflet of the heart valve relative to the surface of the buttress provides substantially unidirectional flow of blood relative to the apparatus.

2. An apparatus as set forth in claim 1, wherein the generally arcuate base portion is a generally C-shaped base portion having a curved length between opposed ends of the C-shaped base portion, the buttress extending from an arc portion of the C-shaped base portion intermediate the opposed ends thereof.

3. An apparatus as set forth in claim 2, wherein the buttress extends a first length in a direction radially inwardly and axially from the base portion and then curves outwardly for a second length thereof.

4. An apparatus as set forth in claim 1, wherein the arcuate base portion is a complete ring and an aperture extends through the apparatus between the buttress and an opposed side of the annular base portion so as to permit substantially bi-directional flow of blood axially relative to the apparatus.

5. An apparatus as set forth in claim 1, wherein the base portion is formed of a generally rigid material.

6. An apparatus as set forth in claim 1, wherein the base portion is formed of a substantially flexible material.

7. An apparatus as set forth in claim 1, further including an outer sheath of a substantially flexible material covering the surface of the buttress.

8. An apparatus as set forth in claim 7, wherein the outer sheath completely covers the buttress and the base portion.

9. An apparatus as set forth in claim 8, wherein the flexible material is a substantially biocompatible animal tissue material.

10. An apparatus as set forth in claim 9, wherein the biocompatible animal tissue material is animal pericardium.

11. An apparatus as set forth in claim 1, further including an implantation flange circumscribing the base portion.

12. An apparatus as set forth in claim 11, wherein the implantation flange is formed of a substantially flexible material.

13. An apparatus as set forth in claim 12, wherein the implantation flange is formed of a substantially biocompatible animal tissue material.

14. An apparatus as set forth in claim 13, wherein the animal tissue material is animal pericardium.

15. An apparatus as set forth in claim 1, further including two elongated posts extending generally axially from the annular base portion for supporting a sheet of flexible material that forms the surface of the buttress, the sheet of flexible material extending from a circumferential arc of the base portion and connecting to each of the two posts.

16. An apparatus as set forth in claim 15, wherein the posts are formed of a generally rigid material.

17. An apparatus as set forth in claim 16, wherein the sheet of flexible material is a substantially biocompatible animal tissue material.

18. An apparatus as set forth in claim 15, wherein each of the posts extend from the base portion and terminate in respective distal ends, the apparatus further including an interconnecting support portion connecting the distal ends of the posts.

19. An apparatus for helping improve operation of a heart valve, comprising:

a frame comprising a generally arcuate base portion and a support portion extending generally axially and inwardly relative to the base portion, the support portion terminating at a distal end spaced from the base portion; and a sheath of a substantially flexible material extending from an arc of the base portion and to the support portion of the frame near the distal end thereof to form a buttress dimensioned and configured to be engaged by at least one leaflet of the heart valve and permit bi-directional flow of fluid axially relative to the apparatus, whereby, when the apparatus is implanted at the heart valve, the at least one leaflet of the heart valve is moveable relative to a surface of the sheath so as to provide for substantially unidirectional blood flow relative to the apparatus.

20. An apparatus as set forth in claim 19, wherein the generally arcuate base portion is a generally C-shaped base portion having a curved length between opposed ends of the C-shaped base portion, the buttress extending from an arc portion of the C-shaped base portion intermediate the opposed ends thereof.

21. An apparatus as set forth in claim 19, wherein the support portion of the frame extends a first length in a direction radially inwardly and axially from the base portion and then curves outwardly for a second length thereof, the sheath of flexible material substantially conforming to the shape of the frame.

22. An apparatus as set forth in claim 19, wherein the arcuate base portion is a complete ring and an aperture extends through the apparatus between the buttress and an opposed side of the annular base portion so as to permit substantially bi-directional flow of blood axially relative to the apparatus.

23. An apparatus as set forth in claim 19, wherein the sheath of flexible material is a substantially biocompatible animal tissue.

24. An apparatus as set forth in claim 23, wherein the biocompatible animal tissue is animal pericardium.

25. An apparatus as set forth in claim 19, further including an implantation flange circumscribing at least a substantial part of the base portion.

26. An apparatus as set forth in claim 19, wherein the support portion of the frame further includes two elongated posts extending generally axially from the annular base portion for supporting the sheath of flexible material extending between the posts to form the surface of the buttress.

27. An apparatus as set forth in claim 26, wherein the posts are formed of a generally rigid material.

28. An apparatus as set forth in claim 26, wherein each of the two posts extend from the base portion and terminate in distal ends, the support portion of the frame further including an interconnecting member connecting the distal ends of the posts.

29. An apparatus for helping improve operation of a defective heart valve having at least one viable leaflet, comprising:

means for supporting an annulus of the heart valve so as to permit bi-directional blood flow through the support means; and means for substantially coapting with the at least one leaflet of the heart valve when the apparatus is attached at the annulus of the heart valve, such that the at least one leaflet is moveable into and out of engagement with the means for substantially coapting to provide for substantially unidirectional blood flow relative to the apparatus, the means for substantially coapting extending from the means for supporting.

* * * * *